(12) United States Patent
Schramm et al.

(10) Patent No.: US 6,909,770 B2
(45) Date of Patent: Jun. 21, 2005

(54) METHODS FOR IDENTIFICATION AND VERIFICATION USING VACUUM XRF SYSTEM

(75) Inventors: Fred Schramm, Winchester, TN (US); Bruce Kaiser, Draper, UT (US)

(73) Assignees: The United States of America as represented by the United States National Aeronautics and Space Administration, Washington, DC (US); Keymaster Technologies, Inc., Kennewick, WA (US)

( * ) Notice: Subject to any disclaimer, the term of this patent is extended or adjusted under 35 U.S.C. 154(b) by 39 days.

(21) Appl. No.: 10/307,191

(22) Filed: Nov. 29, 2002

(65) Prior Publication Data

US 2003/0133537 A1 Jul. 17, 2003

Related U.S. Application Data

(63) Continuation-in-part of application No. 10/006,782, filed on Dec. 5, 2001, now abandoned.

(51) Int. Cl.$^7$ .............................................. G01N 23/223
(52) U.S. Cl. ........................................ 378/45; 378/44
(58) Field of Search ...................................... 378/44–50

(56) References Cited

U.S. PATENT DOCUMENTS

| | | |
|---|---|---|
| 2,957,079 A | 10/1960 | Edholm |
| 4,045,676 A | 8/1977 | Rolle |
| 4,136,778 A | 1/1979 | Wortman et al. |
| 4,251,726 A | 2/1981 | Alvarez |
| 4,363,965 A | 12/1982 | Soberman et al. |
| 4,390,452 A | 6/1983 | Stevens |
| 4,445,225 A | 4/1984 | White |
| 4,476,382 A | 10/1984 | White |
| 4,485,308 A | 11/1984 | Rabatin |
| 4,767,205 A | 8/1988 | Schwartz et al. |

(Continued)

FOREIGN PATENT DOCUMENTS

| | | |
|---|---|---|
| EP | 011627 A1 | 10/1998 |
| EP | 0 911 626 A1 | 10/1998 |
| EP | 0911626 A1 | 10/1998 |
| EP | 0 911 627 A1 | 10/1998 |
| WO | WO0125747 | 4/2001 |

(Continued)

OTHER PUBLICATIONS

Keegan, *Applying Data Matrix Identification Symbols on Aerospace Parts*, NASA Technical Standard NASA–STD–6002, Jul. 2, 2001.

(Continued)

*Primary Examiner*—David V. Bruce
*Assistant Examiner*—Hoon Song
(74) *Attorney, Agent, or Firm*—Kenneth E. Horton; Kirton & McConkie (57) ABSTRACT

Apparatus and methods in which one or more elemental taggants that are intrinsically located in an object are detected by x-ray fluorescence analysis under vacuum conditions to identify or verify the object's elemental content for elements with lower atomic numbers. By using x-ray fluorescence analysis, the apparatus and methods of the invention are simple and easy to use, as well as provide detection by a non line-of-sight method to establish the origin of objects, as well as their point of manufacture, authenticity, verification, security, and the presence of impurities. The invention is extremely advantageous because it provides the capability to measure lower atomic number elements in the field with a portable instrument.

30 Claims, 11 Drawing Sheets

U.S. PATENT DOCUMENTS

| | | | |
|---|---|---|---|
| 4,862,143 A | | 8/1989 | Hirshfield et al. |
| 5,057,268 A | | 10/1991 | Muller |
| 5,185,773 A | | 2/1993 | Blossfeld et al. |
| 5,208,630 A | | 5/1993 | Goodbrand et al. |
| 5,301,044 A | | 4/1994 | Wright |
| 5,461,654 A | | 10/1995 | Grodzins et al. |
| 5,474,937 A | | 12/1995 | Anderson, II et al. |
| 5,527,707 A | | 6/1996 | Fukazawa |
| 5,670,239 A | | 9/1997 | Hampp |
| 5,677,187 A | | 10/1997 | Anderson, II et al. |
| 5,740,223 A | * | 4/1998 | Ozawa et al. ............... 378/161 |
| 5,760,394 A | | 6/1998 | Welle |
| 5,830,769 A | | 11/1998 | Wieder et al. |
| 5,849,590 A | | 12/1998 | Anderson, II et al. |
| 6,005,915 A | | 12/1999 | Hossain et al. |
| 6,007,744 A | | 12/1999 | Nacker |
| 6,024,200 A | | 2/2000 | Jang |
| 6,025,200 A | | 2/2000 | Kaish et al. |
| 6,030,657 A | | 2/2000 | Butland et al. |
| 6,041,095 A | | 3/2000 | Yokhin |
| 6,075,839 A | | 6/2000 | Treseder |
| 6,082,775 A | | 7/2000 | Phillips |
| 6,088,423 A | | 7/2000 | Krug et al. |
| 6,097,785 A | | 8/2000 | Elam |
| 6,106,021 A | | 8/2000 | Phillips |
| 6,111,929 A | | 8/2000 | Hazlett |
| 6,456,729 B1 | | 9/2000 | Moore |
| 6,130,931 A | | 10/2000 | Laurila et al. |
| 6,165,609 A | * | 12/2000 | Curatolo ..................... 428/343 |
| 6,178,226 B1 | | 1/2001 | Hell et al. |
| 6,178,227 B1 | * | 1/2001 | Sato ........................... 378/117 |
| 6,200,628 B1 | | 3/2001 | Rozumek et al. |
| 6,313,423 B1 | | 11/2001 | Sommer et al. |
| 6,477,227 B1 | | 11/2002 | Kaiser et al. |
| 6,501,825 B2 | | 12/2002 | Kaiser et al. |
| 6,533,181 B1 | | 3/2003 | Roxby et al. |
| 6,563,902 B2 | | 5/2003 | Takahashi |
| 6,685,095 B2 | | 2/2004 | Roustaei et al. |

FOREIGN PATENT DOCUMENTS

| | | |
|---|---|---|
| WO | WO0125748 | 4/2001 |
| WO | WO0125763 | 4/2001 |
| WO | WO0125764 | 4/2001 |
| WO | WO0125765 | 4/2001 |
| WO | WO0125766 | 4/2001 |
| WO | WO0125767 | 4/2001 |
| WO | WO0125768 | 4/2001 |
| WO | WO0125820 | 4/2001 |
| WO | WO0125821 | 4/2001 |
| WO | WO0250570 | 6/2002 |
| WO | WO0268945 | 9/2002 |

OTHER PUBLICATIONS

Keegan,*Application of Data Matrix Identification Symbols to Aerospace Parts Using Direct Part Marking Methods/ Techniques*, NASA Technical Handbook NASA–H–DBK–6003, Jul. 2, 2001.

Kaiser et al., PCT application No. PCT/US00/26415, published as WO 01/25820 on Apr. 12, 2001.

Kaiser et al., PCT application No. PCT/US00/26461, published as WO 01/25763 on Apr. 12, 2001.

Kaiser et al., PCT application No. PCT/US00/16784, published as WO 01/025764 on Apr. 12, 2001.

Kaiser et al., PCT application No. PCT/US00/27482, published as WO 02/50570 on Jun. 27, 2002.

Kaiser et al., PCT application No. PCT/US00/27491, published as WO 01/25767 on Apr. 12, 2001 including U.S. Application No. 10/089,671, claiming priority thereof.

Kaiser et al., PCT application No. PCT/US00/27624, published as WO 01/25821 on Apr. 12, 2001 including U.S. Application No. 10/089,872, claiming priority thereof.

Kaiser et al., PCT application No. PCT/US00/27423, published as WO 01/025748 on Apr. 12, 2001 including U.S. Application No. 10/089,870, claiming priority thereof.

Kaiser et al., PCT application No. PCT/US00/27420, published as WO 01/025766 on Apr. 12, 2001 including U.S. Application No. 10/089,671, claiming priority thereof.

Kaiser et al., PCT application No. PCT/US00/27151, published as WO 01/25765 on Apr. 12, 2001.

Kaiser et al., PCT application No. PCT/US00/27492, published as WO 01/25788 on Apr. 12, 2001 including U.S. Application No. 10/089,900, claiming priority thereof.

Kaiser et al., PCT application No. PCT/US00/27418, published as WO 01/025747 on Apr. 12, 2001 including U.S. Application No. 10/089,671, claiming priority thereof.

Kaiser et al., PCT application No. PCT/US02/05219, published as WO 02/068945 on Sep. 6, 2002 including U.S. Application No. 10/006,782, claiming priority thereof.

Co–pending patent application 10/306,923.

U.S. Appl. No. 09/716,625, filed Nov. 20, 2000.

U.S. Appl. No. 09/766,542, filed Jan.19, 2001.

U.S. Appl. No. 10/006,782, filed May 12, 2001.

U.S. Appl. No. 29/144,321, filed Jun. 30, 2001.

U.S. Appl. No. 10/089,671, filed Apr. 02, 2002.

U.S. Appl. No. 10/089,900, filed Aug. 29, 2002.

U.S. Appl. No. 10/089,872, filed Sep. 16, 2002.

U.S. Appl. No. 10/089,870, filed Oct. 08, 2002.

U.S. Appl. No. 10/286,149, filed Nov. 01, 2002.

U.S. Appl. No. 10/306,923, filed Nov. 29, 2002.

U.S. Appl. No. 10/307,191, filed Nov. 29, 2002.

U.S. Appl. No. 10/321,873, filed Dec. 16, 2002.

U.S. Appl. No. 60/459,747, filed Apr. 01, 2003.

U.S. Appl. No. 60/518,577, filed Nov. 07, 2003.

* cited by examiner

METHODS FOR IDENTIFICATION AND VERIFICATION USING VACUUM XRF SYSTEM

REFERENCE TO RELATED APPLICATIONS

This application is a continuation-in-part and claims priority from U.S. patent application Ser. No. 10/006,782, filed Dec. 5, 2001 now abandoned the entire disclosure of which is incorporated herein by reference.

JOINT INVENTION OF GOVERNMENT EMPLOYEE AND NON-FEDERAL PARTY OUTISDE OF ANY FUNDING AGEEMENT OR OTHER ARRANGEMENT

The invention described herein was made in part by an employee of the United States Government and may be manufactured and used by and for the Government of the United States for governmental purposes without the payment of any royalties thereon or therefor.

FIELD OF THE INVENTION

The invention generally relates to apparatus and methods for identification and verification. More particularly, the invention relates to apparatus and methods for detecting an element or elements intrinsically present—or extrinsically added—in an object by using X-ray fluorescence to identify and verify that object. Even more particularly, the invention related to apparatus and methods for detecting an element or compound intrinsically present—or extrinsically added—in an object by using X-ray fluorescence under vacuum conditions.

BACKGROUND OF THE INVENTION

There has been significant interest in apparatus and methods for identifying and verifying various articles or products (or objects) such as explosives, ammunition, paint, petroleum products, and documents. Known methods used to identify and verify such objects generally involve adding and detecting materials like code-bearing microparticles, bulk chemical substances, and radioactive substances. Other methods used for identifying and verifying objects include those described in U.S. Pat. Nos. 6,106,021, 6,082,775, 6,030,657, 6,024,200, 6,007,744, 6,005,915, 5,849,590, 5,760,394, 5,677,187, 5,474,937, 5,301,044, 5,208,630, 5,057,268, 4,862,143, 4,485,308, 4,445,225, 4,390,452, 4,363,965, 4,136,778, and 4,045,676, as well as European Patent Application Nos. 0911626 and 0911627, the disclosures of which are incorporated herein by reference.

It is also known to apply materials to objects in order to track, for example, point of origin, authenticity, and their distribution. In one method, inks that are transparent in visible light are sometimes applied to objects and the presence (or absence) of the ink is revealed by ultraviolet or infrared fluorescence. Other methods include implanting microscopic additives that can be detected optically. However, detecting these materials is primarily based on optical or photometric measurements.

Unfortunately, many of the apparatus and methods for identifying and verifying objects using such materials (called taggants) are unsatisfactory for several reasons. First, they are often difficult and time-consuming. In many instances, a sample of the object (of the object itself) must be sent to an off-site laboratory for analysis. In other instances, the apparatus are often expensive, large, and difficult to operate. In yet other instances, the taggant used is radioactive, causing serious health concerns.

SUMMARY OF THE INVENTION

The invention provides an apparatus and method in which one or more elemental taggants that are intrinsically located in an object are detected by x-ray fluorescence analysis under vacuum conditions to identify or verify the object's elemental content for elements with lower atomic numbers. By using x-ray fluorescence analysis, the apparatus and methods of the invention are simple and easy to use, as well as provide detection by a non line-of-sight method to establish the origin of objects, as well as their point of manufacture, authenticity, verification, security, and the presence of impurities. The invention is extremely advantageous because it provides the capability to measure lower atomic number elements in the field with a portable instrument.

BRIEF DESCRIPTION OF THE DRAWINGS

FIGS. 1, 2a, 2b, 3, 4a, 4b, 5–6, 7a–7b, and 8-10 are views of apparatus and methods for providing x-rays according to the invention, in which:

FIGS. 1, 2a, 2b, 3, 4a, 4b, 5–6, 7a–7b, and 8–10 presented in conjunction with this description are views of only particular—rather than complete—portions of apparatus and methods for providing x-rays according to the invention.

DETAILED DESCRIPTION OF THE INVENTION

The following description provides specific details in order to provide a thorough understanding of the invention. The skilled artisan will understand, however, that the invention can be practiced without employing these specific details. Indeed, the invention can be practiced by modifying the illustrated apparatus and method and can be used in conjunction with apparatus and techniques conventionally used in the industry. For example, the invention is not limited to any specific XRF analysis. Rather, any type of XRF, such as total reflection x-ray fluorescence (TXRF), can be employed in the invention.

The invention uses x-ray fluorescence analysis to detect at least one elemental taggant intrinsically or extrinsically present in the material of an object. With x-ray fluorescence (XRF) analysis, x-rays produced from electron shifts in the inner shell(s) of atoms of the taggants and, therefore, are not affected by the form (chemical bonding) of the article being analyzed. The x-rays emitted from each element bear a specific and unique spectral signature, allowing one to determine whether that specific taggant is present in the product or article.

Figures 1, 2A, 2B:
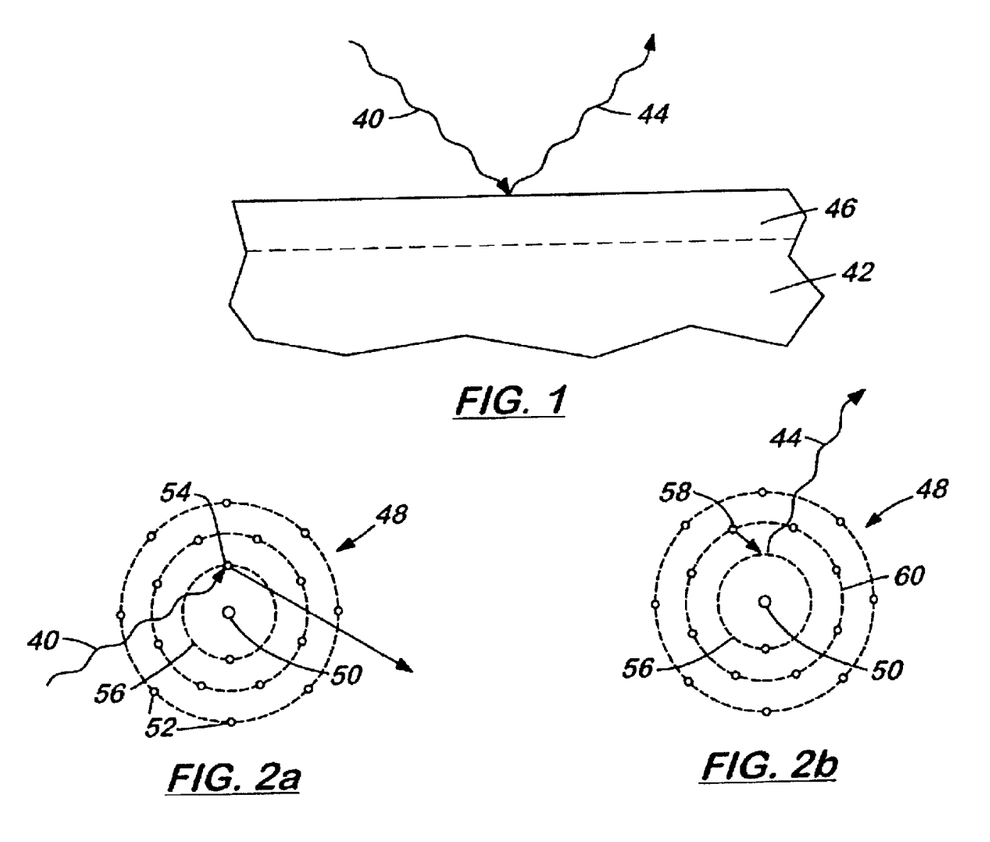
FIG. 1 generally depicts the operation of XRF.
FIGS. 2a and 2b illustrate the operation of XRF at the molecular level.

FIGS. 1, 2a, and 2b represent how it is believed XRF generally operates. In FIG. 1, primary gamma rays or x-rays 40 are irradiated on a sample of a target material 46 of article 42. Secondary x-rays 44 are emitted from that sample of target material 46.

In FIGS. 2a and 2b, atom 48 of a taggant located within target material 46 has nucleus 50 surrounded by electrons 52 at discrete energy bands around the nucleus 50 (called electron shells). Each electron has a binding energy level equal to the amount of energy required to remove that electron from its corresponding shell. The innermost shell is the K shell, and has the highest binding energy levels associated with it. Electron 54 is located within K shell 56.

Primary x-ray or gamma ray photon 40 impacting atom 48 has a given energy. If that energy is greater than the binding energy level of K shell 56, the energy of x-ray photon 40 is absorbed by atom 48, and one of the electrons in K shell 56 (i.e., electron 54) is ejected. With a vacancy now in K shell 56 left by electron 54, atom 48 is energetic and unstable. To become more stable, that vacancy in K shell 56 can be—and usually is—filled by an electron located in a shell with a lower binding energy level, such as L-shell electron 58 in L shell 60. As L-shell electron 58 fills the vacancy in K shell 56, atom 48 emits a secondary x-ray photon 44. The energy levels (or corresponding wavelengths) of such secondary x-ray photons are uniquely characteristic to each elemental taggant, allowing the presence or absence of any specific taggant to be determined.

The taggant can be intrinsically or extrinsically present in the object to be detected (the "target object"). When the taggant(s) is intrinsically present, it is a component (either as an element, compound, or other type of composition) in at least one portion of that target object, such as an impurity. When the taggant(s) is extrinsically present, it can be added, incorporated, or inserted into the target object as described below.

The at least one taggant employed in the invention can be any suitable taggant known in the art. See, for example, U.S. Pat. Nos. 5,474,937, 5,760,394, and 6,025,200, the disclosures of which are incorporated herein by reference. Suitable taggants include any element which is capable of being detected via XRF. The type of elements that can be used as the taggant are theoretically any of those listed in the periodic table, but the lower energy emitted by electrons in the lower atomic-number elements could be a limiting factor. Such lower energies can be re-absorbed much easier into its own material matrix or into the ambient atmosphere (e.g, air). Further, different isotopes of an element, as well as elements which "excite" only under certain conditions could be employed as the taggant in the invention.

Examples of elemental taggants that could be analyzed in the invention include any element with an atomic number ranging from 6 to 94. In the aspect where vacuum conditions are used, the taggants that can be used in the invention include any element with an atomic number ranging from 9 to 17, and especially Al and Si. While materials with these elements typically can be analyzed under laboratory conditions, it has been quite difficult to analyze them under practical conditions in the field.

The type of taggant depends, among other things, on the target object in which it is located. The material of the target object can interfere with the XRF detection because, as described below, backscattering and peaks emitted by the composition of the target object during XRF analysis can interfere with the taggant peaks. For example, if paper (as the target object) contained an As taggant and trace amounts of Pb existed in the paper, the K-level electrons of As and L-level electrons of Pb could give confusing readings during XRF detection.

The amount and concentration of the taggant in the target object can also vary depending on the number of elements used and energy needed. The amount of taggant employed in the invention is determined by the minimum amount needed for XRF detection. Additional amounts of taggant can be used as described below. The concentration of the taggant is at least about 1 part per million (ppm), and can range from about 1–100 ppm. Larger taggant amounts can be used, but for economic reasons, a small amount is sufficient. Even lower taggant concentrations can be used (i.e, less than 1 ppm) as improved XRF devices and techniques become available.

The form of the taggant in the target object can also vary. The form can be any compound (i.e., salt) or molecule—either small or large—containing the element that is added by itself or with other components. Indeed, the taggant can be combined with various components and/or additives to make a mixture and/or solution. These other components or additives can be selected for various purposes, e.g., to modify the XRF properties, to modify the ability to be inserted into the target object, to stabilize the mixture or solution, or other purpose known in the chemical arts.

Any suitable target object can be employed in the invention. Suitable target objects include those which intrinsically contain the desired taggant(s) or in which the desired taggant(s) can be incorporated. Because XRF detection measures changes in the inner shell(s) of the taggant, it will not be significantly modified by chemical reactions that normally occur in the outer shells. Thus, it is possible to tag chemicals and have the taggant code be carried in any object manufactured with those chemicals. Target objects should be comprised of a material in which XRF detection is easy, e.g., little chance of background contamination, taggant deterioration, taggant destruction, contamination, or other deteriorating condition.

Examples of suitable target objects include any manufactured goods or trade goods. Examples of manufactured goods and trade goods are disclosed in U.S. patent application Ser. No. 10/006,782, the entire disclosure of which is incorporated herein by reference. Examples of suitable target objects also include those that will be subsequently changed. For example, a target object that is suspected might be destroyed could be tagged with elements known to be present in the residue from the destruction. Since the taggant is not usually changed by the chemical process in destruction, a connection between the target object and its residue could be established after destruction. Preferably, the target object of the invention is personal identification devices, such as badges, passports, visas, drivers licenses, and swipe tags.

Elemental taggants in the target object(s) can be detected to identify or verify the target material using XRF analysis as illustrated in FIG. 1. Primary x-rays 40 are used to excite a sample of the target material 46, and the secondary x-rays 44 that are emitted by the sample are detected and analyzed.

Figure 3:
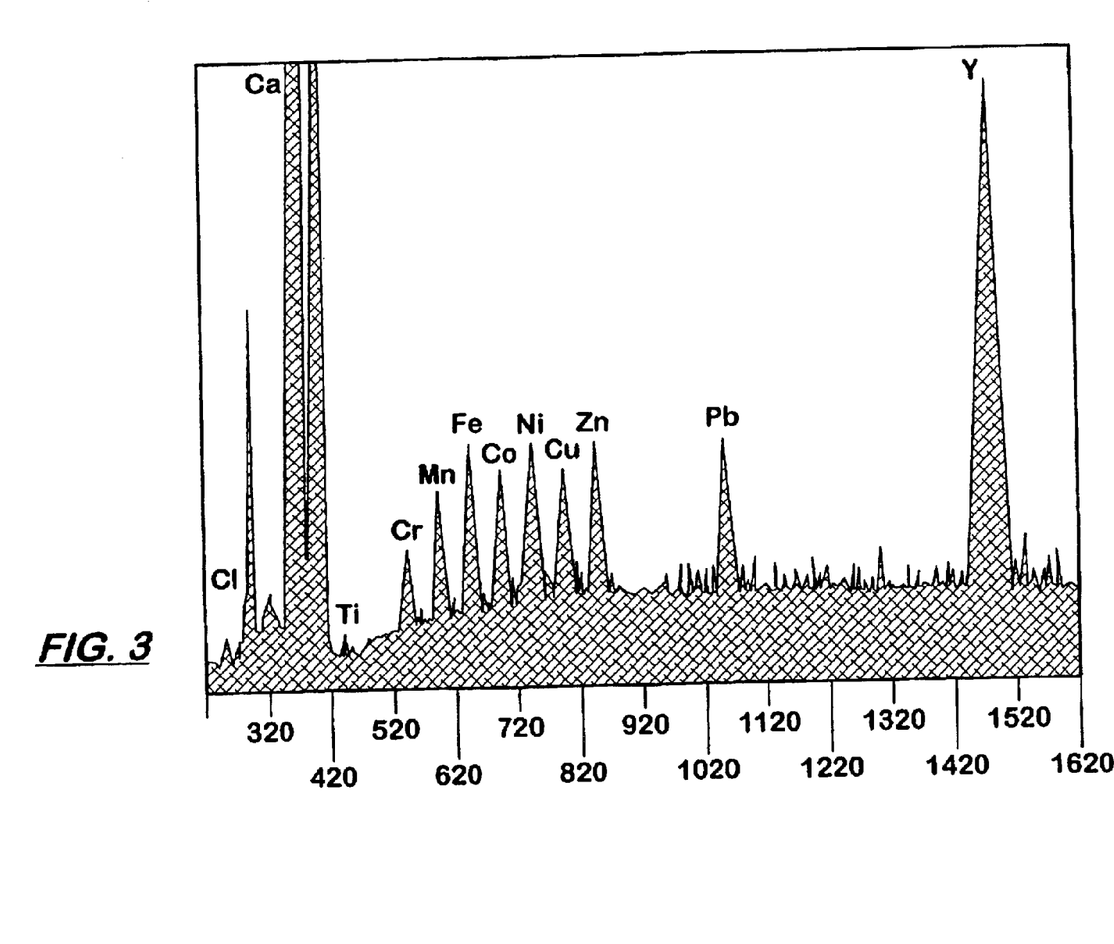
FIG. 3 shows an exemplary x-ray spectrum, e.g., for paper.

As shown in FIG. 3, the x-rays which are detected have various energies, e.g., there is a broad band of scattered x-rays with energies less than and greater than those of the exciting atom. FIG. 3 illustrates this spectrum for paper as the target object. Within this broad band, there are peaks due to the excitation of the taggant(s) in the sample. The ratio of the intensity of the radiation in any peak to the intensity of the background at the same energy (known as the peak-to-background ratio) is a measure of the concentration of the element which has characteristic X-rays at the energy of that peak, e.g., the taggant.

In one aspect of the detection method of the invention, at least one target object believing to contain known concentrations of the taggant(s) of interest is selected. The XRF analysis is performed on that target object (or a sample thereof) using a detection device or apparatus containing an x-ray radiation source ("source"), x-ray radiation detector ("detector"), support means, analyzer means, and calibration means.

Figure 4A:
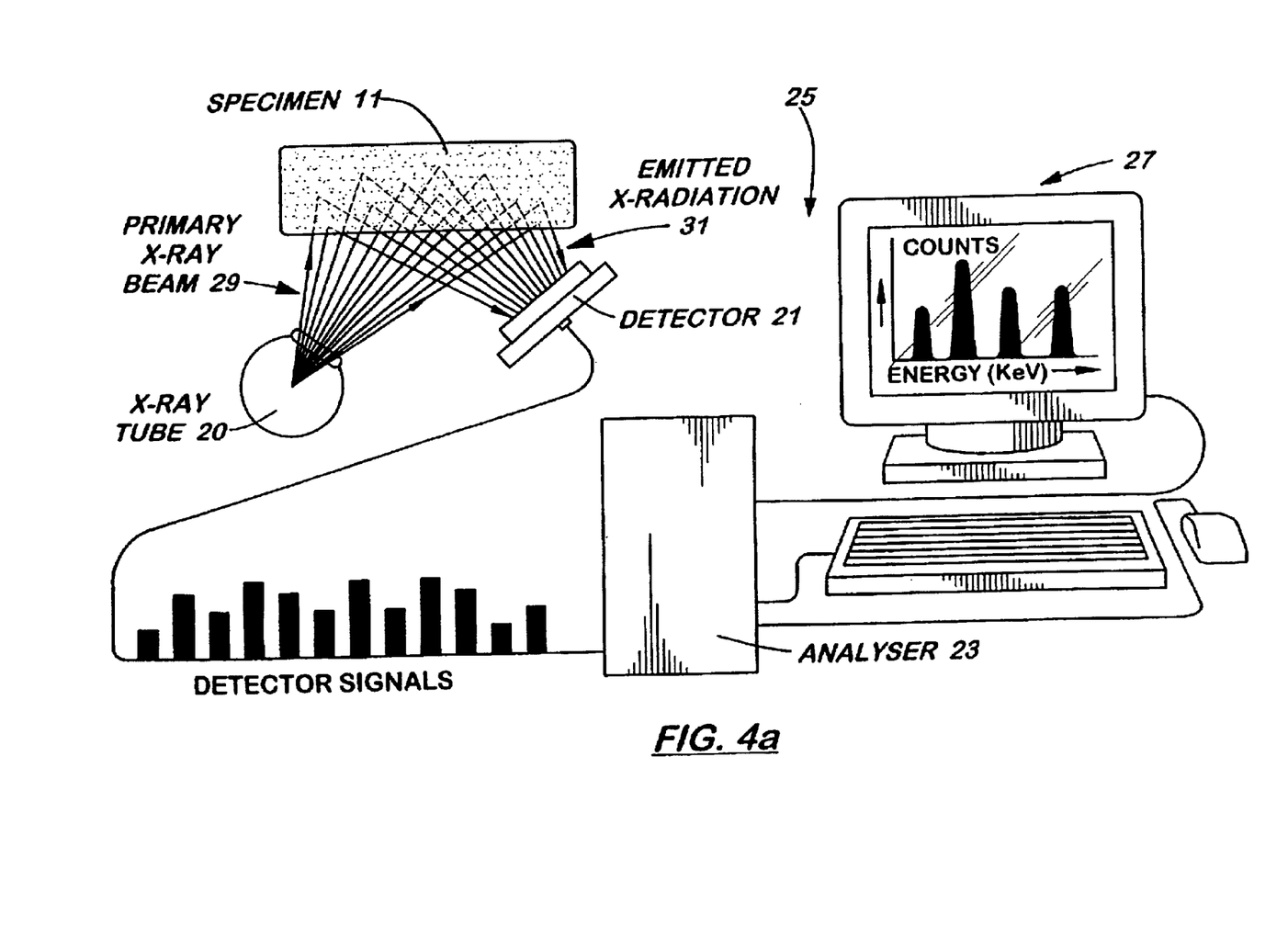
FIGS. 4a and 4b depict two aspects of the of the XRF apparatus of the invention.

One aspect of the detection device of the invention is illustrated in FIG. 4a. In this Figure, the detection apparatus 25 has an ordinary x-ray fluorescence spectrometer capable of detecting elements present in a coating, package or material. X-rays 29 from a source (e.g., either x-ray tube or radioactive isotope) 20 impinge on a sample 11 which absorbs the radiation and emits x-rays 31 to an x-ray detector 21 and analyzer 23 capable of energy or wavelength discrimination. This is accomplished by using a commercially available x-ray spectrometer such as an Edax DX-95 or a MAP-4 portable analyzer, commercially available from Edax Inc., Mahwah, N.J. Part of analyzer 23 includes a computerized system 27.

Figure 4B:
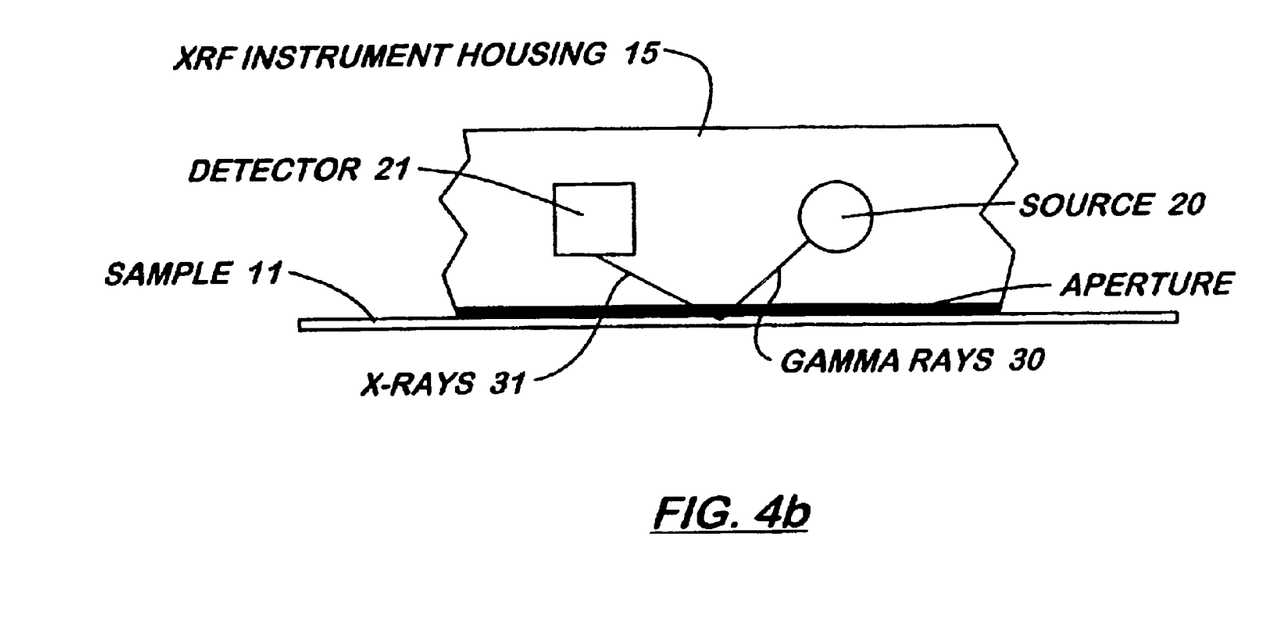

Another aspect of the detection apparatus of the invention is illustrated in FIG. 4b. In this Figure, the detection apparatus 25 has an instrument housing 15 containing the various components. Gamma rays or x-rays 30 from a source (e.g., either x-ray tube or radioactive isotope) 20 are optionally focused by aperture 10 to impinge on a sample 11. Sample 11 contains the at least one taggant which absorbs the radiation and emits x-rays 31 to an x-ray detector 21. Optionally, analyzing means can be incorporated within housing 15.

The invention, however, is not limited to the detection apparatus depicted in FIGS. 4a and 4b. Any suitable source, or plurality of sources, known in the art can be used as the source in the detection device of the present. See, for example, U.S. Pat. Nos. 4,862,143, 4,045,676, and 6,005,915, the disclosures of which are incorporated herein by reference. During the XRF detection process, the source bombards the material with a high energy beam. The beam may be an electron beam or electromagnetic radiation such as X-rays or gamma rays. The source, therefore, may be any material that emits such high energy beams. Typically, these have been x-ray emitting devices such as x-ray tubes or radioactive sources.

To target, the beam can be focused and directed properly by any suitable means such as an orifice or an aperture. The configuration (size, length, diameter . . . ) of the beam should be controlled, as known in the art, to obtain the desired XRF detection. The power (or energy level) of the source should also be controlled, as known in the art, to obtain the desired XRF detection.

The source(s) can be shielded and emit radiation in a space limited by the shape of the shield. Thus, the presence, configuration, and the material used for shielding the source should be controlled for consistent XRF detection. Any suitable material and configuration for that shield known in the art can be employed in the invention. Preferably, any high-density materials used as the material for the shield, e.g, tungsten or brass.

Any suitable detector, or plurality of detectors, known in the art can be used as the detector in the detection device of the invention. See, for example, U.S. Pat. Nos. 4,862,143, 4,045,676, and 6,005,915, the disclosures of which are incorporated herein by reference. Any type of material capable of detecting the photons omitted by the taggant may be used. Silicon and CZT (cadmium-zinc-telluride) detectors have been conventionally used, but others such as proportional counters, germanium detectors, or mercuric iodide crystals can be used.

Several aspects of the detector should be controlled to obtain the desired XRF detection. First, the geometry between the detector and the target material should be controlled. The XRF detection also depend on the presence, configuration, and material—such as tungsten and beryllium—used as a window to allow x-rays photons to strike the detector. The age of the detector, voltage, humidity, variations in exposure, and temperature can also impact the XRF detection and, therefore, these conditions should be controlled.

The analyzer means sorts the radiation detected by the detector into one or more energy bands and measures its intensity. Thus, any analyzer means performing this function could be used in the invention. The analyzer means can be a multi-channel analyzer for measurements of the detected radiation in the characteristic band and any other bands necessary to compute the value of the characteristic radiation as distinct from the scattered or background radiation. See, for example, U.S. Pat. Nos. 4,862,143, 4,045,676, and 6,005,915, the disclosures of which are incorporated herein by reference.

The XRF also depends on the resolution of the x-rays. Background and other noise must be filtered from the x-rays for proper measurement, e.g., the signals must be separated into the proper number of channels and excess noise removed. The resolution can be improved by cooling the detector using a thermoelectric cooler—such as a nitrogen or a peltier cooler—and/or by filtering. Another way to improve this resolution is to use pre-amplifiers.

The support means supports the source and detector in predetermined positions relatively to a sample of the target material to be irradiated. Thus, any support means performing this function could be used in the invention. In one example, the support means comprises two housings, where the source and detector are mounted in a first housing which is connected by a flexible cable to a second housing in which the analyzer means is positioned as illustrated in FIG. 4a. If desired, the first housing may then be adapted to be hand-held. In another example, the source and detector as well as the other components of the detection device are mounted in a single housing as illustrated in FIG. 4b.

The calibration means are used to calibrate the detection apparatus, thus insuring accuracy of the XRF analysis. In this calibration, the various parameters that could be modified and effect the measurement are isolated and calibrated. For example, the geometrical conditions or arrangements can be isolated and calibrated. In another example, the material matrix are isolated and calibrated. Preferably, internal (in situ) calibration during detection is employed as the calibration means in the invention. Components, such as tungsten shielding, are already present to internally calibrate during the XRF analysis. Other methods, such as fluorescence peak or Compton backscattering, could be used for internal calibration in the invention.

Analyzer means, which includes a computerized system 27, is coupled to, receives, and processes the output signals produced by detector 21. The energy range of interest, which includes the energy levels of the secondary x-ray photons 44 emitted by the taggant(s), is divided into several energy subranges. Computerized system 27 maintains counts of the number of X-ray photons detected within each subrange using specific software programs, such as those to analyze the detection and x-ray interaction and to analyze backscatter data. After the desired exposure time, computerized system 27 with display menus stops receiving and processing output signals and produces a graph of the counts associated with each subrange.

Figure 5:
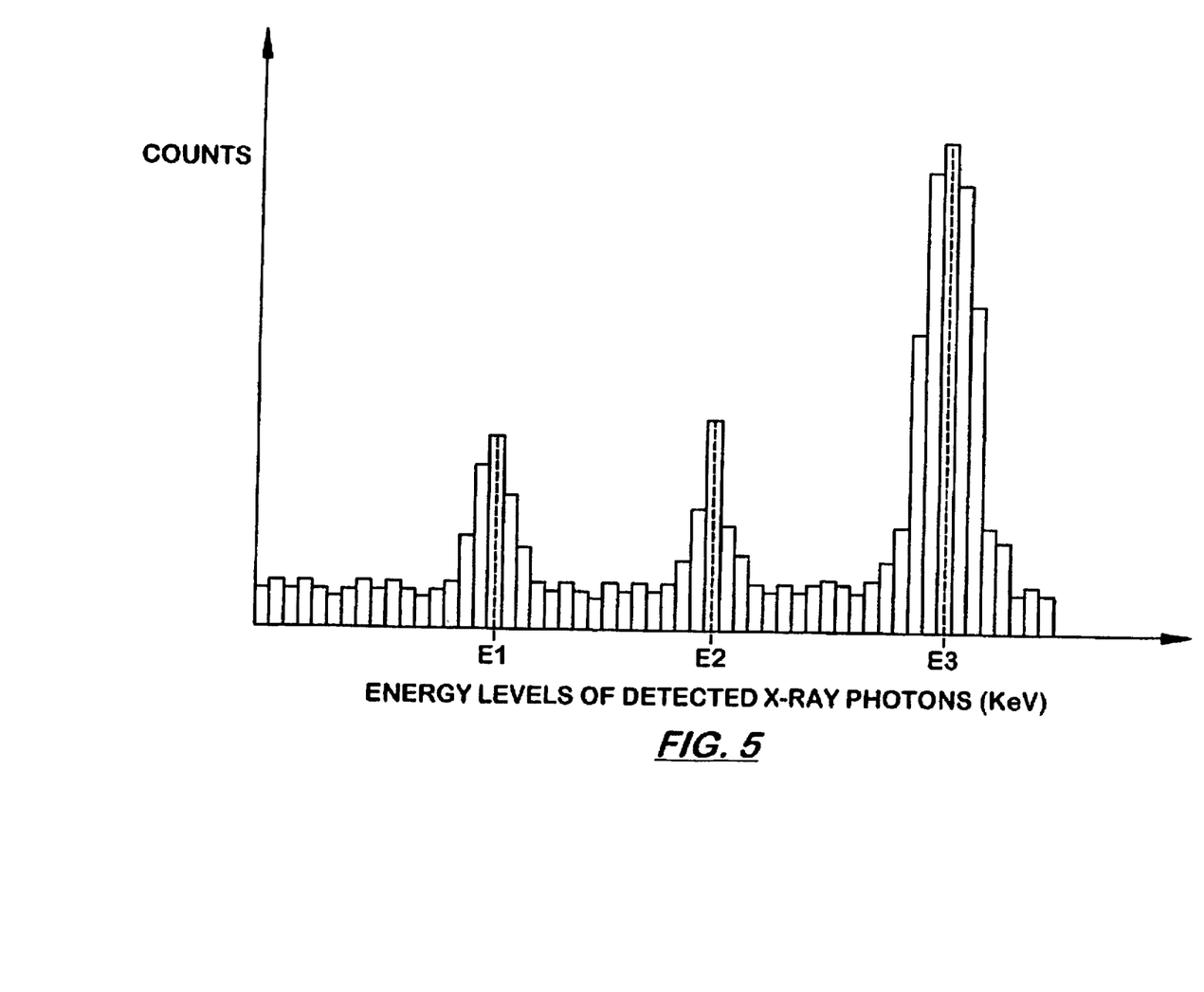
FIG. 5 illustrates exemplary energy levels of x-rays in an x-ray spectrum.

FIG. 5 is a representative graph of the counts associated with each subrange. This graph is essentially a histogram representing the frequency distribution of the energy levels E1, E2, and E3 of the detected x-ray photons. Peaks in the frequency distribution (i.e., relatively high numbers of counts) occur at energy levels of scattered primary x-ray photons as well as the secondary x-ray photons from the taggant(s). A primary x-ray photon incident upon a target material may be absorbed or scattered. The desired secondary x-ray photons are emitted only when the primary x-ray photons are absorbed. The scattered primary x-ray photons reaching the detector of the system create an unwanted background intensity level. Accordingly, the sensitivity of XRF analysis is dependent on the background intensity level, and the sensitivity of XRF detection may be improved by reducing the amount of scattered primary x-ray photons reaching the detector. The peak occurring at energy levels of scattered primary x-ray photons is basically ignored, while the other peaks—those occurring at E1, E2, and E3—are used to identify the at least one taggant present in the target object.

One other parameter that can be controlled during the process of XRF detection is the methods used to interpret and analyze the x-rays. This parameter depends, in large part, on the algorithms and software used along with the apparatus described herein. Thus, methods can be adopted to employ software and algorithms that will consistently perform the XRF detection.

Figure 6:
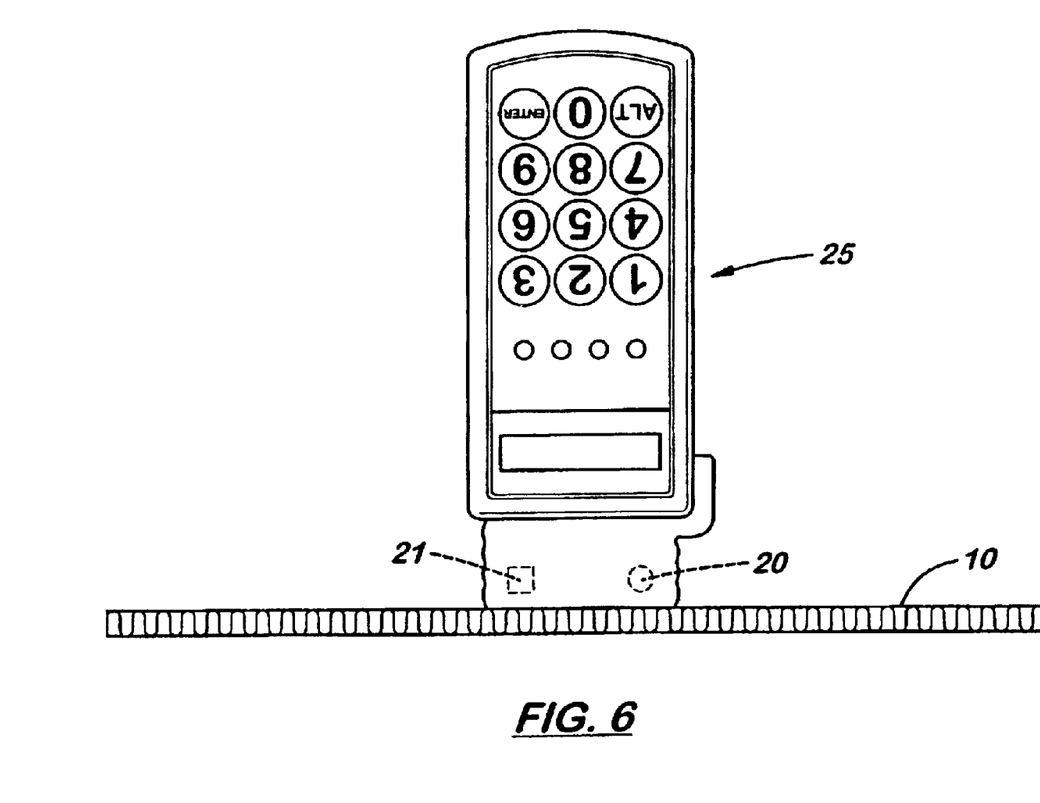
FIG. 6 shows another aspect of the XRF apparatus of the invention.

FIG. 6 illustrates another apparatus and detection method according to the invention. In this Figure, detection apparatus 25 is capable of detecting at least one taggant present in target material 10, such as a document. Detection apparatus 25 is a portable device that can be small enough to be hand-held. Detection apparatus 25 contains all the components discussed above (i.e., source, detector, analyzer means, and calibration means) in a single housing, thus allowing the portability and smaller size.

In one aspect of the invention, the apparatus and method used identify an object or article. The ability to read an elemental taggant that may not be visible provides an invaluable asset in any industry that authenticates, verifies, tracks, labels, or distributes goods of any kind. Thus, the inventions could analyze liquid flows and metal sheets for contaminant particles or pinpoint via 3-D analysis the exact location of a contaminant(s) in an article.

In one aspect of the invention, the methods and apparatus described above can be modified to operate under vacuum conditions. As described above, XRF analysis and XRF apparatus can be limited in terms of the type of elements that can be used as the taggant. While XRF can theoretically analyze any element listed in the periodic table, the lower energy emitted by electrons in the lower atomic-number elements can be reabsorbed much easier into its own material matrix or, in some cases, into the ambient atmosphere (e.g., air). Thus, the ability for XRF to analyze such elements is not extremely efficient. By operating under a vacuum, these lower energies are not absorbed into the air.

To perform XRF under vacuum conditions, the apparatus described above is modified so that the detection operation is carried out in a vacuum. Any such modification achieving this function can be employed in the invention, including the modifications described below.

Figure 7A:
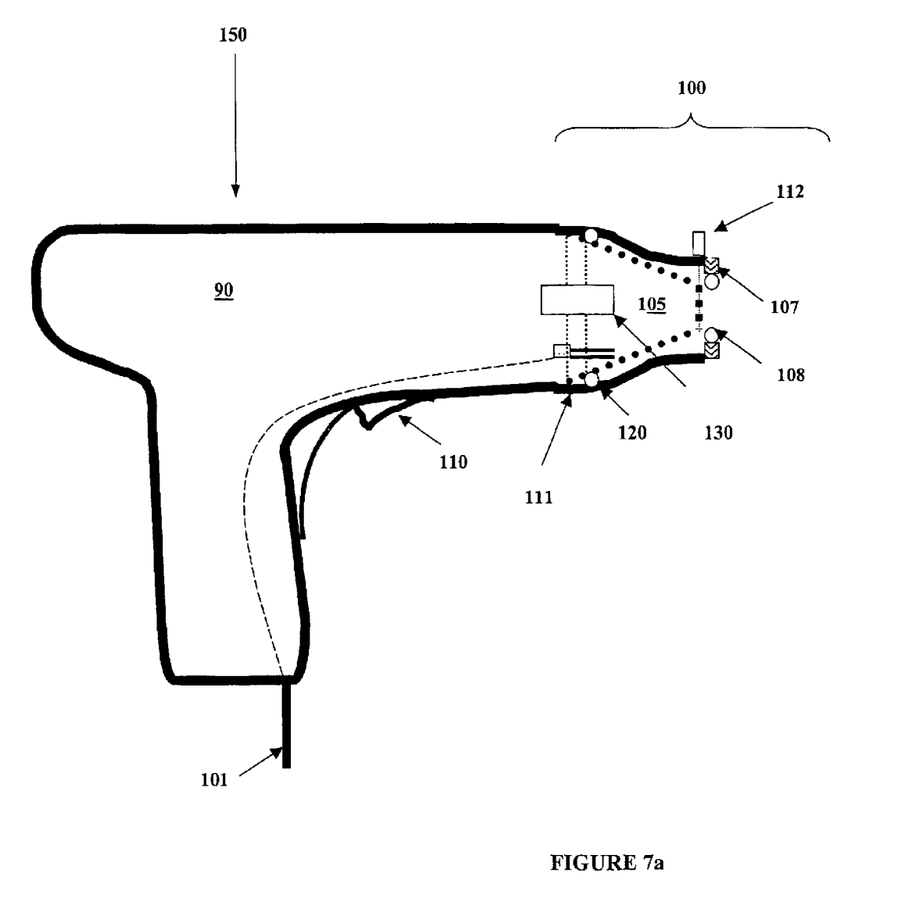
FIGS. 7a and 7b show another aspect of the XRF apparatus of the invention.
Figure 7B:
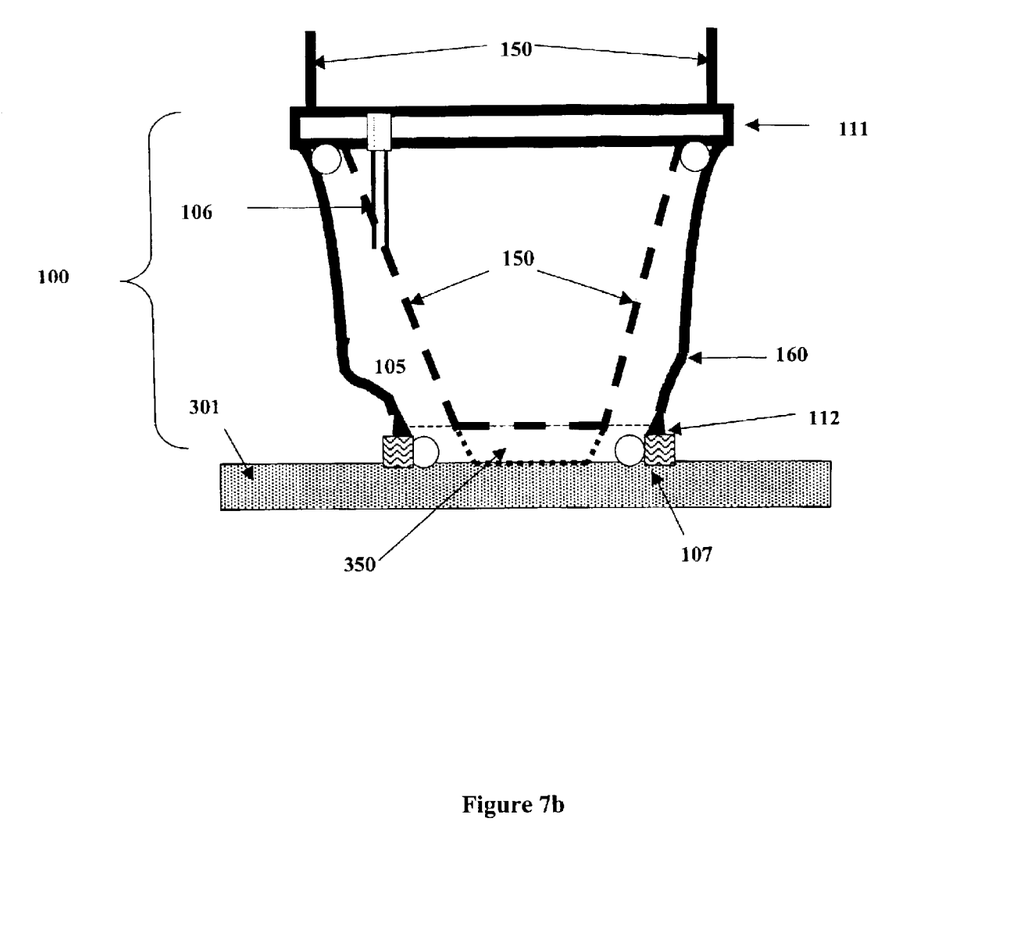

In one aspect, the "vacuum" XRF (VXRF) apparatus 90 used in the invention is depicted in a side view in FIG. 7a and an end view in FIG. 7b. In these Figures, a hand-held XRF device 150 (such as alluded to in FIG. 6 and as described in U.S. Pat. No. D460,370, the entire disclosure of which is incorporated herein by reference) is fitted with a vacuum attachment 100. The vacuum attachment 100 creates vacuum conditions for device 150 in the front end where detection of the taggant occurs.

The vacuum attachment (VA) 100 contains all the necessary components to create a vacuum on the end of device 150. In the aspect of the invention illustrated in FIG. 7a, the vacuum attachment 100 contains a vacuum line 101, vacuum chamber 105, vacuum port 106, seal flange 107, and seal 108. All of these components are combined to create the vacuum conditions at the end of device 150. Other (or alternative) components that are necessary to create and maintain the vacuum can be used in the invention as known in the art.

The vacuum attachment 100 contains a quick disconnect 111 removable front end with an aperture sized to the desired exposure area to be detected. The VA 100 also contains a shutter device 112 that is used to isolate the vacuum chamber 105 when the vacuum conditions are cycled on and off. The VA 100 also contains seals 120 where the VA 100 attaches to the device 150, as well as latches 130 for securely attaching the VA 100 to device 150. Other (or alternative) components that are necessary to aid operation of the vacuum can be used in the invention as known in the art.

Figure 8:
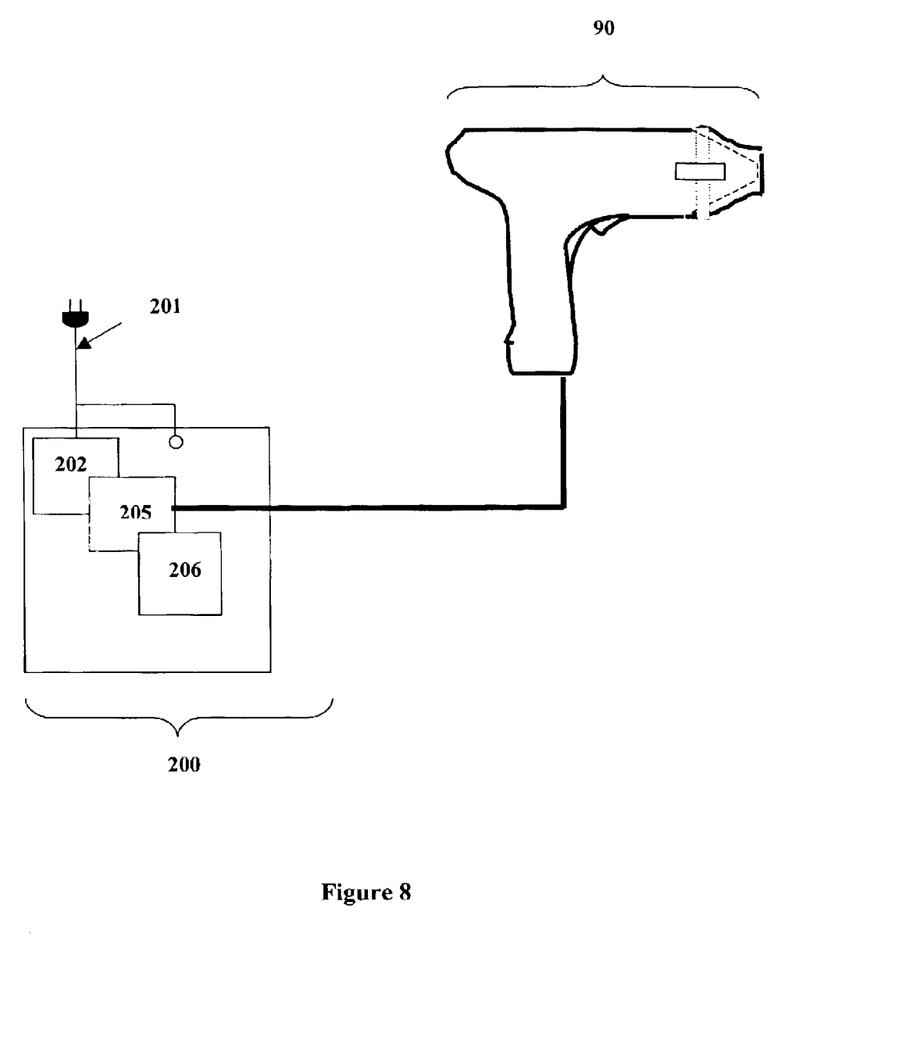
FIG. 8 shows another aspect of the XRF apparatus of the invention.

The VXRF device 90 also contains components that are used to create and control the vacuum. As depicted in FIG. 8, VRXF 90 comprises a controller 200 that is connected to a standard 110 volt outlet 201. The controller 200 contains a grounded power supply 202, a vacuum pump 205, and a timer 206 that sequences the operation of the pump 205. Other (or alternative) components that are necessary to create and control the vacuum can be used in the invention as known in the art.

The VA 100 in combination with the device 150 operates in the following manner. As shown in FIG. 7b, VA 100 on the device 150 is originally in a position that is not depressed. The VA 100 can then be depressed into position 350 to contact a substrate 301 and to engage the seal mechanism 107 to form an airtight compartment 105. After depressing the device to the surface of the substrate 301 using flexible member 160, a trigger 110 is depressed to activate a timer 206 that controls the air evacuation process. The vacuum pump 205 then draws the ambient air out of the chamber 105 through the vacuum port 106, leaving a clear path of access for the device 150 to contact the surface of substrate 301. After creating the vacuum, the XRF 150 remains pressed to contact the surface in position 350 for the amount of time needed for the XRF analysis. After finishing the XRF analysis, the vacuum pump 205 is turned off and the VA attachment is then slowly removed.

The VXRF apparatus 90 can create any desired vacuum condition that is necessary to analyze the taggant being analyzed. In one aspect of the invention, the VXRF apparatus 90 can create a vacuum ranging from about 1 to about $10^{-7}$ torr. In another aspect of the invention, VXRF apparatus 90 can create a vacuum ranging from about 1 to about $10^{-2}$ torr. Under these conditions, the VXRF apparatus 90 can more efficiently detect and analyze taggants containing elements with periodic numbers of 9 to 17.

The following non-limiting example illustrates the invention.

EXAMPLE

Figure 9:
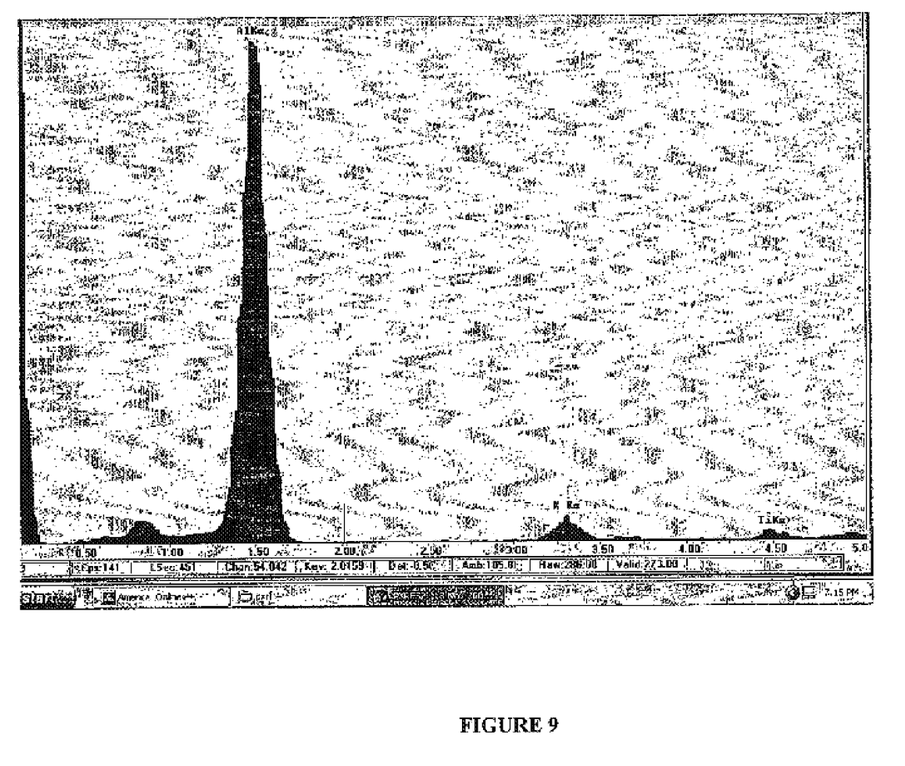
FIGS. 9 and 10 depict the x-ray spectrum produced by the invention when analyzing a sample containing Al and Mg.
Figure 10:
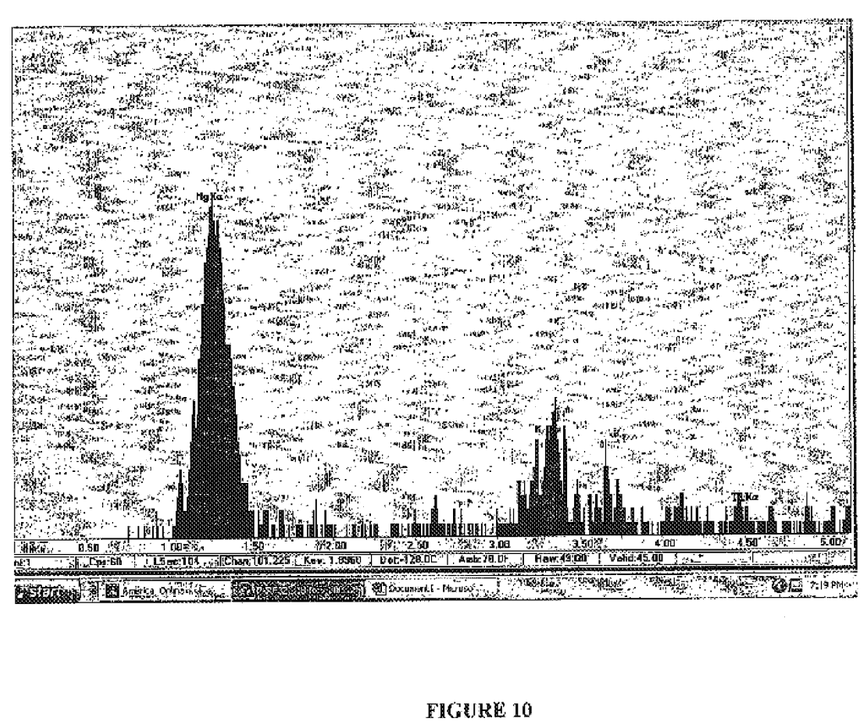

A first sample of a $\frac{1}{16}^{th}$ inch aluminum sheet and a second sample of Mg metal were obtained. A hand-held XRF device similar to that depicted in U.S. Pat. No. D460,370 was made to contain an x-ray source and a peltier-cooled silicon detector. Vacuum conditions were created at the front end of the XRF device. The XRF device was then used to analyze the first and second samples while under the vacuum. FIGS. 9 and 10 depict the resulting x-ray spectrum for the first and second sample, respectively.

Having described the preferred aspects of the invention, it is understood that the invention defined by the appended claims is not to be limited by particular details set forth in the above description, as many apparent variations thereof are possible without departing from the spirit or scope thereof.

We claim:

1. A method for detecting a taggant in an object using x-ray fluorescence in a vacuum, comprising:
   providing an object comprising a taggant containing an element with an atomic number ranging from 9 to 17;
   making a vacuum x-ray fluorescence device by providing an x-ray fluorescence device with a vacuum attachment;
   creating a vacuum the adjacent to the object using the vacuum x-ray fluorescence device;
   causing the taggant to radiate an x-ray through the vacuum by irradiating the taggant with an x-ray; and
   analyzing through the vacuum whether the x-ray has a specific energy.

2. The method of claim 1, wherein the object is a manufactured good or a trade good.

3. The method of claim 1, wherein the vacuum ranges from about 1 to about $10^{-7}$ torr.

4. The method of claim 1, wherein the vacuum ranges from about 1 to about $10^{-2}$ torr.

5. The method of claim 1, including providing the taggant in a concentration less than about 100 ppm.

6. The method of claim 1, including providing a plurality of taggants with different concentrations.

7. The method of claim 1, including providing the taggant with different concentrations.

8. The method of claim 1, wherein the x-ray fluorescence device is a hand-held device.

9. The method of claim 1, wherein the vacuum attachment comprises means for creating a vacuum and means for maintaining the vacuum.

10. The method of claim 9, wherein the vacuum attachment comprises means for restraining the vacuum attachment to the x-ray fluorescence device.

11. A vacuum attachment for a hand-held x-ray fluorescence device, comprising:
    a vacuum chamber;
    means for sealing the vacuum chamber to a substrate containing a taggant to be analyzed;
    means for restraining the vacuum chamber near the region of a detector in an x-ray fluorescence device;
    means for creating a vacuum in the vacuum chamber;
    means for controlling the vacuum; and
    means for the vacuum chamber to communicate with the creating means and the controlling means.

12. The device of claim 11, wherein the communicating means comprises a vacuum port.

13. The device of claim 11, wherein the communicating means comprises a vacuum line.

14. The device of claim 11, wherein the sealing means comprises a seal flange and a seal bead.

15. The device of claim 11, wherein the restraining means comprises latches.

16. The device of claim 11, further comprising sealing means between the vacuum chamber and the x-ray fluorescence device.

17. The device of claim 11, further comprising means for isolating the vacuum chamber when creating the vacuum.

18. The device of claim 11, wherein the means for creating the vacuum includes a vacuum pump.

19. The device of claim 11, wherein the means for controlling the vacuum includes a timer.

20. A hand-held vacuum x-ray fluorescence device, comprising:
    an x-ray fluorescence device containing a source and a detector; and
    a vacuum attachment containing:
      a vacuum chamber;
      means for sealing the vacuum chamber to a substrate to be analyzed;
      means for restraining the vacuum chamber near the region of the detector;
      means for creating a vacuum in the vacuum chamber;
      means for controlling the vacuum; and
      means for the vacuum chamber to communicate with the creating means and the controlling means.

21. The device of claim 20, wherein the communicating means comprises a vacuum port.

22. The device of claim 20, wherein the communicating means comprises a vacuum line.

23. The device of claim 20, wherein the sealing means comprises a seal flange and a seal bead.

24. The device of claim 20, wherein the restraining means comprises latches.

25. The device of claim 20, further comprising sealing means between the vacuum chamber and the x-ray fluorescence device.

26. The device of claim 20, further comprising means for isolating the vacuum chamber when creating the vacuum.

27. The device of claim 20, wherein the means for creating the vacuum includes a vacuum pump.

28. The device of claim 20, wherein the means for controlling the vacuum includes a timer.

29. A method for detecting a taggant in an object using a portable vacuum x-ray fluorescence device, comprising:
    providing an object comprising a taggant;
    providing a portable vacuum x-ray fluorescence device;
    creating a vacuum near the object using the portable vacuum x-ray fluorescence device;
    causing the taggant to radiate an x-ray through the vacuum by irradiating the taggant with an x-ray; and
    analyzing through the vacuum whether the x-ray has a specific energy.

30. The method of claim 29, including providing the portable vacuum x-ray fluorescence device by providing a portable x-ray fluorescence device with a vacuum attachment.

* * * * *